United States Patent [19]

Niedballa et al.

[11] Patent Number: 4,570,007
[45] Date of Patent: Feb. 11, 1986

[54] 2-AMINO-1-(1,2-DIOXOLAN-4-YL)ETHANOL COMPOUNDS, THEIR PREPARATION AND USE

[75] Inventors: Ulrich Niedballa; Heinz Gries, both of Berlin, Fed. Rep. of Germany

[73] Assignee: Shering Aktiengesellschaft, Berlin and Berghaman, Fed. Rep. of Germany

[21] Appl. No.: 722,088

[22] Filed: Apr. 11, 1985

Related U.S. Application Data

[63] Continuation of Ser. No. 451,375, Dec. 20, 1982, abandoned.

[30] Foreign Application Priority Data

Dec. 18, 1981 [DE] Fed. Rep. of Germany ....... 3150917

[51] Int. Cl.$^4$ ................ C07D 317/00; C07D 317/72
[52] U.S. Cl. .................................. 549/451; 549/341; 549/449; 564/153; 564/156
[58] Field of Search ............ 549/341, 449, 451; 564/153, 156

[56] References Cited

U.S. PATENT DOCUMENTS

| | | | |
|---|---|---|---|
| 2,606,908 | 8/1952 | Blicke | 549/451 |
| 3,701,771 | 10/1972 | Almen et al. | |
| 3,981,891 | 9/1976 | Celli et al. | 549/333 |
| 4,001,323 | 1/1977 | Felder et al. | |
| 4,021,481 | 5/1977 | Almen et al. | |
| 4,352,788 | 10/1982 | Felder et al. | 424/5 |

FOREIGN PATENT DOCUMENTS 0033426 8/1981 European Pat. Off.

OTHER PUBLICATIONS

Chemical Abstracts 96:68970d (1981).

*Primary Examiner*—Ethel G. Love
*Attorney, Agent, or Firm*—Millen & White

[57] ABSTRACT

2-Amino-1-(1,3-dioxolan-4-yl)ethanol compounds of formula (I)

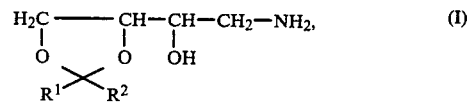

wherein $R^1$ and $R^2$ are identical or different and can be hydrogen or a lower alkyl group of 1-4 carbon atoms; or when $R^2$ is an alkyl group of 1-4 carbon atoms, $R^1$ can also be an alkoxy group of 1-4 carbon atoms; or $R^1$ and $R^2$ combined form an alkylene residue of 5 or 6 carbon atoms, are especially suited as intermediates in the production of opacifying compounds useful in X-ray contrast media.

7 Claims, No Drawings

2-AMINO-1-(1,2-DIOXOLAN-4-YL)ETHANOL COMPOUNDS, THEIR PREPARATION AND USE

This is a continuation of application Ser. No. 451,375 filed Dec. 20, 1982, now abandoned.

BACKGROUND OF THE INVENTION

This invention relates to new compounds useful, inter alia, as intermediates for preparation of pharmacologically useful compounds.

Small, highly substituted hydrophilic amines are frequently employed industrially, for example as aids in the textile, leather, and papers industries, as raw materials for detergents, as solubilizing substituents in pharmaceuticals, etc. Of maximum importance is their use in the synthesis of X-ray contrast media. In this case, a basic molecular substrate, highly substituted with iodine atoms for the purpose of X-ray absorption, is further substituted with hydrophilic residues to ensure water solubility and physiological compatibility. These substituents, by their structure, have a decisive influence on these properties of the X-ray contrast media.

The synthesis of novel X-ray contrast media thus is frequently dependent on the availability of new, suitable intermediates which when combined as substituents impart to the basic component the desired characteristics. Since most X-ray diagnostic techniques require the use of relatively large amounts of contrast medium, it is also necessary to manufacture the X-ray contrast medium and its requisite intermediates conveniently and economically.

It is especially advantageous to effect the linkage between the iodine-containing basic component and the hydrophilic substituent by way of an amide bond. This bond is stable and, due to its polarity, likewise contributes toward rendering the entire molecular water-soluble.

Many examples of this type of compound can be found in the literature. Also, this acyl function is included in multiple form. Thus, Belgian Pat. No. 836,355 (or U.S. Pat. No. 4,001,323) discloses the synthesis of 5-(α-hydroxypropionylamino)-2,4,6-triiodoisophthalic acid N,N'-bis(1,3-dihydroxyprop-2-yl)diamide(iopamidol), while the synthesis of metrizamide[2-(3-acetamido-5-N-methylacetamido-2,4,6-triiodobenzamido)-2-deoxy-D-glucose] is described in DOS No. 2,031,724 (or U.S. Pat. No. 3,701,771). Both compounds have been introduced commercially.

European Application No. 0,033,426 discloses 5-acetamido-2,4,6-triiodoisophthalic acid N,N'-bis(1,3,4-trihydroxybut-2-yl)diamide, as well as 2,4,6-triiodotrimesic acid N,N',N"-tris(1,3,4-trihydroxybut-2-yl)triamide, both of which contain 2-amino-1,3,4-butanetriol as the amine component.

In the reactions described therein, iodinated basic components are utilized. These carry one or several acid chloride groups. The latter are reacted with an alkylamine substituted by hydroxy groups.

The high hydrophilicity desired in the final product X-ray contrast medium proves, however, to be a disadvantage in the preparation of these compounds. Such compounds are hard to purify due to their low tendency toward crystallization as well as their poor solubility in aprotic, low-boiling solvents.

The purity of the final products and thus also the cost of the ultimate purification is decisively affected by the reaction speed with which the acid chloride and the amine react. The speed is higher in the case of an aminomethyl group —$CH_2$—$NH_2$ than for a sterically hindered amine. For this reason, those amines are found to be most suitable for the synthesis of X-ray contrast media wherein the amino group is not sterically hindered, and the hydroxy groups are entirely or partially blocked.

For example, aminotrihydroxybutane exists as four isomeric compounds:

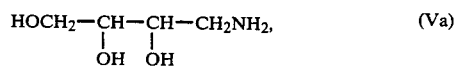
(Va)

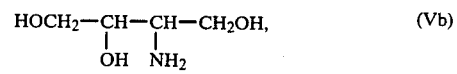
(Vb)

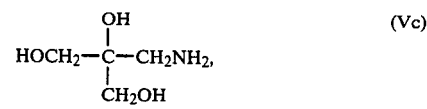
(Vc)

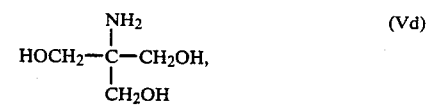
(Vd)

When using it as the hydroxylated alkylamine in the synthesis, compound Va will be most advantageous for reaction with an acid chloride since the amino group is least hindered sterically. However, since its primary hydroxy group can likewise react with the acid chloride and can lead to secondary products, it is expedient to utilize compound Va as an intermediate I wherein the hydroxy groups are blocked.

Similar amines are also used in European Patent Application No. 0,033,426; such as, for example, compounds of Formula (VI)

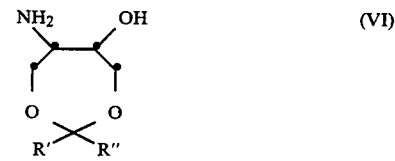
(VI)

However, these compounds have the crucial disadvantage that they contain a sterically hindered amino group

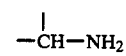

requiring more drastic reaction conditions than an aminomethylene group —$CH_2$—$NH_2$. They lead to by-products, making the purification of the final products problematic. Additionally, since the compounds of Formula (VI) are dioxepanes, they represent a sterically stressed 7-membered ring system which, as experience has shown, is less stable with respect to a weakly acidic medium than a 5-membered ring system. By premature cleavage of blocking groups, these compounds increase the danger of the occurrence of by-products.

SUMMARY OF THE INVENTION

Accordingly, it is an object of the present invention to provide new intermediates which overcome or ameliorate the foregoing disadvantages.

Upon further study of the specification and appended claims, further objects and advantages of this invention will become apparent to those skilled in the art.

These objects have been achieved by providing 2-amino-1-(1,3-dioxolan-4-yl)ethanol compounds of Formula (I)

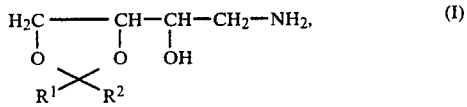

wherein $R^1$ and $R^2$ are identical or different, and each is hydrogen or a lower alkyl group of 1–4 carbon atoms; or when one is an alkyl group of 1–4 carbon atoms, the other can be alkoxy of 1–4 carbon atoms; or $R^1$ and $R^2$ together can form alkylene of 5 or 6 carbon atoms.

DETAILED DISCUSSION

The amines of Formula (I) of this invention possess a reactive, hardly hindered amino group $-CH_2-NH_2$, permitting shorter reaction periods during acylation. This is of importance especially for the reaction of sensitive compounds since fewer by-product are obtained. The blocking group for the 3,4-positioned hydroxy groups present in the compounds of Formula (I), is of adequate stability to survive, without premature cleavage, the reaction conditions used in further processing to iodine-containing X-ray contrast media. However, if necessary and when desired, they can be readily split with methods known to those skilled in the art, for example by means of dilute aqueous mineral acids under slight heating, or at room temperature.

The amines of Formula (I) according to this invention are excellently suited for the preparation of the opacifying compounds of X-ray contrast media by reacting an iodine-containing acid chloride or bisacid chloride to form the corresponding iodine-containing monoamide or bisamide. Thus, it is possible, for example, to prepare 5-[N-(2-hydroxyethyl)acetylamino]-2,4,6-triiodoisophthalic acid bis(2,3,4-trihydroxybut-1-yl)diamide, an opacifying compound with excellent compatibility and water solubility, using an amine of Formula (I) by the following method. This X-ray contrast agent, its preparation and use are all disclosed in commonly assigned U.S. application Ser. No. (451,374), filed on even date, now U.S. Pat. No. 4,547,357, whose entire disclosure is incorporated by reference herein.

1(A) 5-Acetylamino-2,4,6-triiodoisophthalic Acid Bis(2,3,4-trihydroxybut-1-yl)diamide Within 15 minutes, a solution of 51 g (80 mmol) of 5-acetylamino-2,4,6-triiodoisophthalic acid dichloride in 100 ml of dimethylacetamide is added dropwise under slight cooling and agitation at room temperature to a solution or suspension of 180 mmol of 2-amino-1-(2,2-dimethyl-1,3-dioxolan-4-yl)ethanol in 100 ml of dimethylacetamide. Thereafter 25.1 ml (180 mmol) of triethylamine is added dropwise thereto. After agitation overnight, the suspension is heated for 4 hours to 50° C., then cooled and acidified with 4.5 ml of aqueous concentrated hydrochloric acid. After several hours, the thus-precipitated triethylamine hydrochloride (about 22 g, 90% of theory) is vacuum-filtered, and the filtrate is extensively concentrated under vacuum. This residue is combined with 200 ml of water and 4 ml of aqueous concentrated sodium hydroxide solution (about pH=10), and stirred for several hours. With this aqueous-acidic and aqueous-alkaline treatment, blocking groups present in the amide residues are generally split off quantitatively, which is tested by thin-layer chromatography. Otherwise the blocking groups are cleaved by repeated aqueous-acidic treatment. The resultant solution is treated with 500 ml of cation exchanger IR 120, and the eluate is concentrated under vacuum. After stirring with water and refluxing with ethanol, 47.8 g (74% of theory) of 5-acetylamino-2,4,6-triiodoisophthalic acid bis(2,3,4-trihydroxybut-1-yl)diamide is obtained, mp 279°–283° C. (decomposition).

Iodine, calculated 47.17%, found 47.32%.

In place of 2-amino-1-(2,2-dimethyl-1,3-dioxolan-4-yl)ethanol, any other compound of Formula (I) may be used analogously to prepare the X-ray contrast agent. The iodine-containing starting compound is known and conventionally preparable; see, e.g., the mentioned U.S. application Ser. No. 451,374, U.S. Pat. Nos. 3,701,771 and 4,021,481 (Compound No. 11 of Table 4 and 5) and Eur. Appln. No. 0.033,426 whose entire disclosures are incorporated by reference herein.

As mentioned above, the compounds of Formula (I), if desired, make is possible to isolate the reaction product of (I) with the respective acid chloride before splitting off the hydroxy blocking group, because the blocked group is sufficiently stable for this purpose. Since these intermediate products with the preserved blocked hydroxy group possess lower polarity than the polyhydroxy compounds formed therefrom by blocking group cleavage, these compounds can be isolated more readily and purified by washing, recrystallization, or chromatography.

Routine cleavage of the blocking groups, which takes place following isolation or purification, then yields the polyhydroxy compound. The following operating method exemplifies this.

1(B) 5-Acetylamino-2,4,6-triiosoisophthalic Acid Bis[2-hydroxy-2-(2,2-dimethyl-1,3-dioxolan-4-yl)ethyl]diamide As described under 1(A), 180 mmol of 2-amino-1-(2,2,-dimethyl-1,3-dioxolan-4-yl)ethanol is reacted with 51 g (80 mmol) of 5-acetylamino-2,4,6-triiodoisophthalic acid dichloride, and the reaction mixture, prior to adding 4.5 ml of aqueous concentrated hydrochloric acid, is worked up according to the following directions:

The resultant suspension is filtered off, the filtrate evaporated to dryness under vaccum, the evaporation residue is thoroughly extracted under agitation with acetone, then with methylene chloride, and finally with water to which ammonia has been added to pH 9.

Yield: 38.5 g (54.2% of theory) of 5-acetylamino-2,4,6-triiodoisophthalic acid bis[2-hydroxy-2-(2,2-dimethyl-1,3-dioxolan-4-yl)ethyl]diamide, mp 277°–278° C.

If this compound is used to conduct the acidic treatment with concentrated hydrochloric acid and the subsequent working-up process as described in the directions under 1(A), the product is 5-acetylamino-2,4,6-triiodoisophthalic acid bis(2,3,4-trihydroxybut-1-yl)diamide disclosed under 1(A).

2. 5-[N-(2-Hydroxyethyl)acetylamino]-2,4,6-triiodoisophthalic Acid Bis(2,3,4-trihydroxybut-1-yl)diamide A methylate solution from 100 ml of methanol and 2.48 g (108 mmol) of sodium is combined with 110 ml of 1,2-propylene glycol, 40.3 g (50 mmol) of 5-acetylamino-2,4,6-triiodoisophthalic acid bis(2,3,4-trihydroxybut-1-yl)diamide, and, for rewashing, with 50 ml of methanol. During agitation and heating to 50° C., a solution is produced from which the methanol is distilled off under vacuum. The solution is then combined with 6.7 ml (100 mmol) of 2-chloroethanol and further stirred for 5 hours at 50° C. After cooling, the suspension is combined with one liter of acetone and filtered after one hour. The precipitate, which contains sodium chloride, is again extracted with acetone and vacuum-filtered. This mixture (about 47 g) is dissolved in 470 ml of water and passed over a column with 600 ml of cation exchanger IR 120. The aqueous eluate is exhaustively concentrated under vacuum, the residue is taken up in 370 ml of water and analogously treated with the anion exchanger IRA 410, and worked up. Extraction of the residue by boiling with 165 ml of isopropanol yields 27.6 g (64.7% of theory) of the title compound, mp 283°-287° C. (decomposition).

Iodine, calculated 44.73%, found 44.2%.

The invention also relates to a process for the preparation of 2-amino-1-(1,3-dioxolan-4-yl)ethanol compounds of Formula (I), comprising conventionally (a) reacting a 1,3-dioxolane epoxide of Formula (II)

$$\text{H}_2\text{C} \underset{\underset{R^1 \diagup\diagdown R^2}{O \qquad O}}{\overline{\qquad}} \text{CH}\text{—}\text{CH}\underline{\qquad}\text{CH}_2, \quad \text{(II)}$$

wherein $R^1$ and $R^2$ are as defined above, with $NH_3$; or (b) hydrogenating an azide compound of Formula (III)

$$\text{H}_2\text{C} \underset{\underset{R^1 \diagup\diagdown R^2}{O \qquad O}}{\overline{\qquad}} \text{CH—CH—CH}_2\text{—N}_3, \quad \text{(III)}$$
$$\qquad\qquad\qquad\quad \text{OH}$$

wherein $R^1$ and $R^2$ are as defined above.

In order to prepare the compounds of Formula (I) of this invention by following process version (a), the corresponding 1,2-oxido compound of Formula (II) is heated in a suitable polar solvent, such as water, dimethylformamide, or a similar solvent, with excess ammonia at a temperature of 80°-140° C., preferably 100°-130° C., in a pressurized vessel until the oxido ring has been completely opened, whereafter the product is worked up and purified by crystallization.

The 1,2-oxido compound of Formula (II) required for this reaction can be obtained according to methods known to persons skilled in the art, for example according to the following scheme:

$$\text{HOCH}_2\text{—CH=CH—CH}_2\text{OH} \xrightarrow{\text{HOCl}} \quad \text{(II)}$$

$$\text{HOCH}_2\text{—CH—CH—CH}_2\text{OH} \xrightarrow{\overset{R_1 \diagup R_2}{\underset{O}{\overset{C}{\|}}\atop Cl}} $$
$$\qquad\qquad\;\;\;\;|$$
$$\qquad\qquad\;\;\;\text{OH}$$

$$\underset{\underset{R^1 \diagup\diagdown R^2}{O \quad\; O}}{\text{CH}_2\text{—CH—CH—CH}_2\text{OH}} \xrightarrow{OH^\ominus} \underset{\underset{R^1 \diagup\diagdown R^2}{O \quad\; O}}{\text{CH}_2\text{—CH—CH}\underline{\quad}\text{CH}_2}$$
$$\;\;\;\;\;\;|\qquad\qquad\qquad\qquad\qquad\qquad\qquad\qquad\quad\;\; \diagdown\!\!\diagup$$
$$\;\;\;\;\;\text{Cl}\qquad\qquad\qquad\qquad\qquad\qquad\qquad\qquad\qquad\;\;\; O$$

($R^1$ and $R^2$ are as defined above.)

The process will be described in greater detail using as an example the preparation of 2-(2,2-dimethyl-1,3-dioxolan-4-yl)ethylene oxide (a compound of Formula (II) wherein $R^1=R^2=CH_3$):

1. [W. Reppe et al., Liebigs Ann. Chem. 596: 137 (1955)].

Under vigorous agitation and cooling to 0°-5° C., 150 g of chlorine is introduced within 6 hours into a solution of 182 g of cis-1,4-dihydroxy-2-butene and 288 g of crystallized soda ($Na_2CO_3 \times 10H_2O$). The mixture is stirred for another hour, concentrated under vacuum at 50°-55° C., and diluted with 0.6 l of ethanol. After standing overnight, the mixture is filtered off from sodium chloride and thoroughly washed with ethanol. The solution and the filtrate are concentrated, thus obtaining 3-chloro-1,2,4-butanetriol as a yellow oil.

Yield: 272 g (97% of theory) of 3-chloro-1,2,4-butanetriol.

2. Within 2 hours, 258 ml of 2,2-dimethoxypropane is added dropwise to a stirred and water-cooled solution of 272 g of 3-chloro-1,2,4-butanetriol and 0.5 ml of concentrated sulfuric acid in 1 liter of acetone. The reaction is completed after another 4 hours. The solution is neutralized by the addition of 3.8 g of barium hydroxide, stirred for 30 minutes, filtered off from the solid matter, and concentrated to dryness under vacuum, yielding 2-chloro-2-(2,2-dimethyl-1,3-dioxolan-4-yl)ethanol as a yellow oil.

Yield: 340 g (94% of theory).

3. 340 g of 2-chloro-2-(2,2-dimethyl-1,3-dioxolan-4-yl)ethanol is dissolved in 1.5 l of absolute ether. At 5° C., a total of 130 g of pulverized potassium hydroxide is added under intensive agitation within 30 minutes, while the temperature is maintained between 5° and 15° C. by cooling. The suspension is then heated at 40° C. for 2 hours under gentle refluxing. After heater and agitator have been turned off, the phases begin to separate. After allowing the mixture to stand overnight, it is vacuum-filtered over kieselguhr. The residue is extracted with ether. The combined ether extracts are concentrated over a 60 cm Vigreux column. The residue (260 g) is distilled under vacuum, during which step 180 g of a colorless liquid passes over; this liquid is fractionated, yielding 2-(2,2-dimethyl-1,3-dioxolan-4-yl)ethylene oxide at 65° C./13 mm.

Yield: 154.5 g (57% of theory).

If the compounds of Formula (I) are produced in accordance with process version (b), the starting compound is the corresponding azide of Formula (III) which is hydrogenated according to methods also known to those skilled in the art. Thus, it is possible, for example, to convert the azide compound III into the amine of Formula (I) in a suitable solvent, such as, for example, methanol, ethanol, or with hydrogen in the presence of a noble metal catalyst, such as palladium/charcoal, for example. This reaction can also be conducted by producing the required hydrogen in the presence of the azide compound III for example by the use of hydrazine hydrate and Raney nickel in a suitable solvent, such as methanol/ethanol, or by heating the mixture to boiling, thus obtaining the amine of Formula (I).

The starting compounds of Formula III necessary for process version (b) are obtained according to the following reaction scheme ($R^1$ and $R^2$ are as defined above):

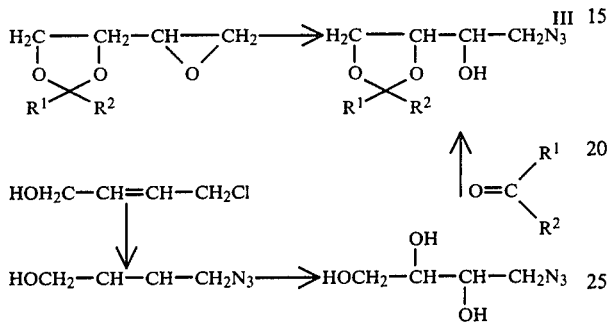

The following production methods exemplify these reactions:

2-Azido-(2,2-dimethyl-1,3-dioxolan-4-yl)ethanol

A. 4.23 g of sodium azide is dissolved in a mixture of 50 ml of water and 100 ml of dioxane. The solution is heated to 60° C., 8.65 g of 2-(2,2-dimethyl-1,3-dioxolan-4-yl)ethylene oxide in 10 ml of dioxane is added dropwise thereto, and the mixture is heated for 2 hours to 80° C. After cooling, the aqueous phase is saturated with sodium chloride. The organic phase is separated, dried over sodium sulfate, and concentrated to dryness under vacuum. The residue is distilled with a water-jet aspirator. 2-Azido-(2,2-dimethyl-1,3-dioxolan-4-yl)ethanol passes over at 130°-132° C./13 mm as a colorless oil. Yield: 9.1 g (81% of theory).

B(1) 4-Azidobut-2-enol

Under agitation, 10.65 g of 4-chlorobut-2-enol is added dropwise within 20 minutes to a solution, heated to 60° C., of 7.8 g of sodium azide in a mixture of 50 ml of water and 70 ml of dioxane. The mixture is stirred for 16 hours at 60° C., concentrated to dryness under vacuum, and distilled under vacuum. 4-Azidobut-2-enol passes over at 72°-73° C./14 mm as a colorless oil. Yield: 8.71 g (77% of theory).

B(2) 4-Azido-1,2,3-butanetriol

Under thorough agitation, a solution of 700 mg of tungsten trioxide in 11.3 ml of perhydrol is added dropwise to a solution, heated to 70° C., of 11.3 g of 4-azidobut-2-enol in 90 ml of water. After 3 hours, no peroxide can be detected any longer with acidified potassium iodide solution. The tungstic acid is removed by adding alkaline ion exchanger. The solution is concentrated to dryness under vacuum. The residue is a viscous oil. Yield: 13.1 g (83% of theory).

B(3) 2-Azido-(2,2-dimethyl-1,3-dioxolan-4-yl)ethanol

A solution of 14.71 g of 4-azido-1,2,3-butanetriol in 30 ml of acetone is combined with 13.95 g of 2,2-dimethoxypropane, as well as 0.1 ml of concentrated sulfuric acid. The mixture is stirred overnight at room temperature, neutralized with 2N sodium hydroxide solution, and concentrated to dryness under vacuum. The residue is distilled with a water-jet aspirator. 2-Azido-(2,2-dimethyl-1,3-dioxolan-4-yl)ethanol passes over as a colorless oil at 130°-132° C./13 mm. Yield: 11.79 g (63% of theory).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A solution of 73.4 g of 2-(2,2-dimethyl-1,3-dioxolan-4-yl)ethylene oxide in 400 ml of aqueous ammonia (25% strength) is heated for 4 hours to 130° C. in an autoclave. The slightly yellowish solution is evaporated to dryness under vacuum. The residue crystallizes. Recrystallization from ethanol/ether yields 2-amino-1-(2,2-dimethyl-1,3-dioxolan-4-yl)ethanol, mp 94°-96° C. Yield: 52.8 g (64.2% of theory).

EXAMPLE 2

A solution of 9.36 g of 2-azido-1-(2,2,-dimethyl-1,3-dioxolan-4-yl)ethanol in 150 ml of methanol is combined with 900 mg of palladium/charcoal catalyst (10%). The hydrogenation is conducted for 1 hour under normal pressure. The mixture is then filtered off from the catalyst and washed with methanol. The combined solutions are concentrated to dryness under vacuum. The remaining oil is crystallized from ethanol/ether, thus obtaining 6.29 g (78% of theory) of 2-amino-1-(2,2-dimethyl-1,3-dioxolan-4-yl)ethanol in white needles, mp 94°-96° C.

EXAMPLE 3

A solution of 9.36 g of 2-azido-1-(2,2-dimethyl-1,3-dioxolan-4-yl)ethanol in 50 ml of ethanol is combined with 4.2 g of hydrazine hydrate and a spatula tip of Raney nickel (about 200 mg). The mixture is then heated to boiling under agitation with very vigorous generation of gas, which ends after 20 minutes. The cooled solution is freed of catalyst by filtration and concentrated to dryness under vacuum. The oily residue is crystallized from ethanol/ether, thus obtaining 2-amino-1-(2,2-dimethyl-1,3-dioxolan-4-yl)ethanol in the form of white needles.

Yield: 6.69 g (83% of theory), mp 94°-96° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 2-amino-1-(1,3-dioxolan-4-yl)ethanol compound of the formula

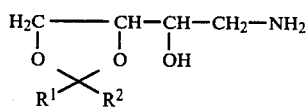

wherein $R^1$ and $R^2$ are identical or different and each is hydrogen or alkyl of 1-4 carbon atoms; or when one is alkyl of 1-4 carbon atoms, the other can also be alkoxy of 1-4 carbon atoms; or $R^1$ and $R^2$ together form alkylene of 5 or 6 carbon atoms.

2. 2-amino-1-(1,3-dioxolan-4-yl)ethanol, a compound of claim 1.

3. 2-amino-1-(2-methyl-1,3-dioxolan-4-yl)ethanol, a compound of claim 1.

4. 2-amino-1-(2,2-dimethyl-1,3-dioxolan-4-yl)ethanol, a compound of claim 1.

5. A compound of claim 1 wherein $R^1$ and $R^2$ together form alkylene of 5 or 6 carbon atoms.

6. A compound of claim 1 wherein at least one of $R^1$ and $R^2$ is alkyl.

7. A method of preparing 5-[N-(2-hydroxyethyl)acetylamino]-2,4,6-triiodoisophthalic acid bis(2,3,4-trihydroxybut-1-yl)diamide comprising, reacting 5-acetylamino-2,4,6-triiodoisophthalic acid or acid dichloride with a 2-amino-1-(1,3-dioxolan-4-yl)ethanol of claim 1 and cleaving the OH blocking groups on the portion derived from 2-amino-1-(1,3-dioxolan-4-yl)ethanol followed by reacting the resultant 5-acetylamino-2,4,6-triiodoisophthalic acid bis(2,3,4-trihydroxybutyl)diamide with 2-chloroethanol.

* * * * *